United States Patent [19]

Blaschke et al.

[11] 4,416,808
[45] Nov. 22, 1983

[54] BIS-BETAINE-AMINE OXIDES, PROCESS FOR THEIR PREPARATION, AND CLEANING AGENTS CONTAINING THEM

[75] Inventors: Günter Blaschke, Winhöring; Alwin Reng, Kelkheim; Jochen M. Quack, Eppstein, all of Fed. Rep. of Germany

[73] Assignee: Hoechst Aktiengesellschaft, Fed. Rep. of Germany

[21] Appl. No.: 439,732

[22] Filed: Nov. 8, 1982

[30] Foreign Application Priority Data

Nov. 19, 1981 [DE] Fed. Rep. of Germany ....... 3145734

[51] Int. Cl.³ .................... C07C 79/16; C11D 1/75; C11D 1/90; C11D 7/32
[52] U.S. Cl. ................................. 252/547; 252/527; 252/528; 252/546; 252/DIG. 5; 260/501.13; 564/294; 564/297; 564/298; 568/704; 568/712
[58] Field of Search ......... 252/546, 547, 527, DIG. 5, 252/528; 260/501.13; 564/294, 297, 298; 568/712, 704

[56] References Cited

U.S. PATENT DOCUMENTS

| | | | |
|---|---|---|---|
| 3,028,415 | 4/1962 | Nordgern | 260/465.5 |
| 3,366,671 | 1/1968 | Cowen et al. | 260/501.13 |
| 3,615,797 | 10/1971 | Ohtsuka et al. | 106/278 |
| 3,660,460 | 5/1972 | Munakata et al. | 260/464 |
| 3,819,539 | 5/1974 | Bloch et al. | 260/501.13 X |

*Primary Examiner*—John E. Kittle
*Assistant Examiner*—Mukund J. Shah
*Attorney, Agent, or Firm*—Connolly and Hutz

[57] ABSTRACT

Bis-betaine-amine oxides of the formula

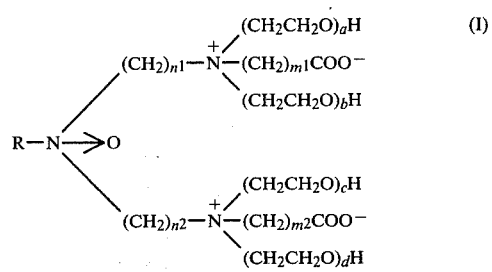

in which
R is a saturated or an olefinically unsaturated hydrocarbon radical having 1 to 3 double bonds and 8 to 22 carbon atoms,
$n^1$ and $n^2$ each is an integer of from 2 to 3, $n^1$ and $n^2$ optionally being identical or different,
$m^1$ and $m^2$ each is an integer of from 1 to 4, $m^1$ and $m^2$ optionally being identical or different, and
a, b, c and d, being identical or different, each is a number of from 1 to 5, with the proviso that the sum (a+b+c+d) is at most 10.

The compounds are prepared from primary amines of the formula $RNH_2$, by dicyanoalkylation, hydrogenation, ethoxylation, reaction with alkali metal salts of ω-halocarboxylic acids, and subsequent oxidation with hydrogen peroxide. They are surfactants of mild action and suitable for formulating cosmetic and industrial cleaning agents.

4 Claims, No Drawings

BIS-BETAINE-AMINE OXIDES, PROCESS FOR THEIR PREPARATION, AND CLEANING AGENTS CONTAINING THEM

The human skin and hair are contaminated by exogenous and endogenous impurities, mainly pigments such as ferric oxides, silicon dioxide, carbon black, oils and greases (sebum), their oxidation and degradation products, and microorganisms. For removing these impurities, surfactant-containing solutions or dispersions are generally used, especially surfactants having an anionic, nonionic, amphoteric or, possibly, cationic structure. Most commonly used agents for skin and hair cleaning are soaps, alkyl sulfates, alkyl ether sulfates, alkylbenzene sulfates or alkylsulfonates, either alone or in corresponding combinations. Most of the agents are characterized by a pronounced cleaning action. On washing with the above surfactants, the user often applies an overdose; the result is a too severe degreasing of hair and skin surface which manifests itself in a poor combability of the hair and an unpleasant dry, taut feeling of skin and scalp. Simultaneously, the skin feels unpleasantly "tacky" after the washing due to the adsorption of the anionic surfactants, and after long-time application of such surfactants the skin has a rough surface full of chaps.

Attempts have already been made to overcome these disadvantages by adding cationic surfactants, but the formation of electrically neutral salts between anionic and cationic surfactants frequently brings about turbidities or precipitations in the formulations. The addition of substances which are polymeric and cationic also frequently causes problems due to reduced foam formation and too high an adsorption on the hair, which leads to an unpleasant accumulation effect. The result is a "greasy" handle of the hair just washed.

Even amphoteric surfactants having a betaine group in the molecule have been tried, either on their own or combined with anionic surfactants. German Auslegeschrift No. 1,249,433 describes, for example, the use of alkylbetaines in cleaning agents, while amidoalkylbetaines of the formula $R^1CONH.(CH_2)_x.N^+R^2R^3.(CH_2)_y.COO^-$, in which $R^1$ is the alkyl radical of a fatty acid have been recommended as skin-compatible bath additives, in German Auslegeschrift No. 1,172,802, and as germicidal hair washes which do not irritate the eyes, in German Auslegeschrift No. 1,062,392. However, the surfactant action of these mono-betaines is inadequate. In addition, the alkylbetaines, for example, have poor compatibility with the mucous membrane of the eye and even that of the amidoalkylbetaines is still not optimal.

In order to solve all these problems, there is a great demand for so-called mild surfactants having a less pronounced cleaning effect, which meet the recent requirements of short washing intervals, thus allowing an increased frequency of hair washing or shower bathing. The gentle cleaning effect simultaneously compensates the overconcentration of the surfactant solutions usual in the practice.

In accordance with the invention, there are provided for this purpose bis-betaine-amine oxides of the formula

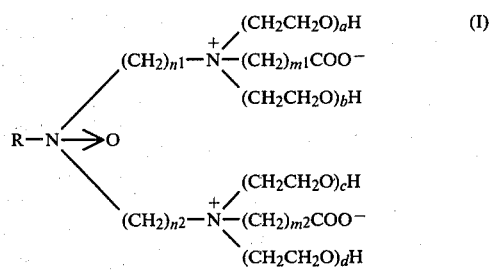

in which
R is a saturated or an olefinically unsaturated hydrocarbon radical having 1 to 3 double bonds and 8 to 22 carbon atoms,
$n^1$ and $n^2$ each is an integer of from 2 to 3, $n^1$ and $n^2$ optionally being identical or different,
$m^1$ and $m^2$ each is an integer of from 1 to 4, $m^1$ and $m^2$ optionally being identical or different, and
a, b, c and d, being identical or different, each is a number of from 1 to 5, with the proviso that the sum (a+b+c+d) is at most 10.

In these bis-betaine-amine oxides according to the invention, of the formula I, the radical R has 8 to 22 carbon atoms, it can be saturated or unsaturated with 1 to 3 olefinic double bonds, and it can be straight-chain or branched. These alkyl or alkenyl radicals, which originate in the primary starting amine in the preparation of bis-betaine-amine oxides of the invention, are frequently mixtures or fractions of particular chain lengths, preferably with the chain distribution of the radicals of natural fatty acids, such as, in particular, the coconut, tallow or palm kernel fatty acid, from which these starting amines can be obtained via the path of nitrile hydrogenation or ammonolysis of the corresponding alcohols. The alcohols used for preparing the primary amines by means of ammonolysis can be not only fatty alcohols but also those which have a straight or branched chain from the Ziegler process (alcohols obtained by the growth reaction from ethylene) or from the oxo synthesis.

To prepare compounds according to the invention, such a primary amine of the formula $RNH_2$ (II) in which R has the above meaning is first reacted with 2 mols of at least one reactive nitrile of 2 to 3 carbon atoms (including the CN group) to give a compound of the formula

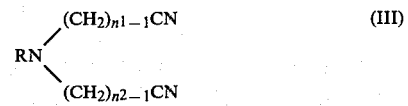

in a dicyanoalkylation reaction. This reaction is known, for example from U.S. Pat. No. 3,028,415. It can be carried out not only with acidic but also with basic catalysis, with the aid of solvents, such as water or low-molecular weight alcohols, unpressurized or under an elevated pressure, in a continuous or discontinuous manner. Acidic catalysts mentioned are acetic acid, phosphoric acid, hydrochloric acid and other mineral acids (U.S. Pat. Nos. 3,615,797 and 3,028,415 and German Offenlegungsschrift 1,941,913), and basic catalysts which have been recommended are sodium hydroxide potassium hydroxide, alkali metal alcoholates, trimethylbenzylammonium hydroxide and morpholine (Kirk- Othmer, Encyclopedia of Chemical Technology, 1965, Volume 6, page 634 et seq.; and H. A. Bruson "Cyanoethylation", Organic Reactions, 5, 1949, page 79 et seq., published by John Wiley and Sons, New York). Water or lower alcohols, such as methanol, ethanol, isopropanol or mixtures of the same, are added as co-catalysts or also as solubilizers in amounts of 1 to 20% by weight. The dicyanoalkylation is carried out under atmospheric pressure or a slight to medium overpressure of 1 to 20 bar, optionally in the presence of an inert gas, at temperatures of 60° to 150° C. The cyanoalkylating agent, preferably acrylonitrile or chloroacetonitrile, is used stoichiometrically or in up to four-fold excess.

The dikcyanoalkylation product (III) thus obtained is then reduced in the presence of hydrogen to give a compound of the formula

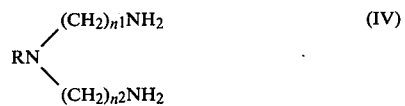

(IV)

which is then condensed with ethylene oxide to give a compound of the formula

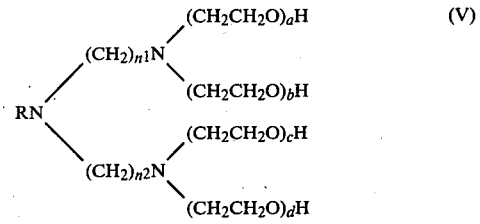

(V)

The two reactions are likewise known for obtaining the compounds at issue (cf. U.S. Pat. No. 3,615,797, already mentioned above). The reduction is carried out by means of Raney nickel or Raney cobalt or by means of supported nickel or cobalt catalysts, namely with the use of 1 to 10% by weight of catalysts, preferably 1 to 5% by weight, under pressures of 50 to 200 bar of hydrogen and at temperatures of 60° to 150° C.; the time for this reaction is about 1 to 5 hours.

The ethoxylation reaction is carried out in pressure vessels, namely at an elevated temperature within a range of 110° to 170° C. and under an elevated pressure of 1 to 5 bar. A catalyst is not required if, preferably, only one ethylene oxide unit is to be added per chain. If a catalyst is used, ethylene oxide chains which contain more than one unit are preferentially obtained. 4 to 10 mols of ethylene oxide are used per 1 mol of compound IV in the reaction, preferably 4 to 5 mols. In the addition, the ethylene oxide can be diluted with an inert gas.

The ethylene oxide addition product thus obtained is then reacted in known manner to give the bis-betaine of the formula

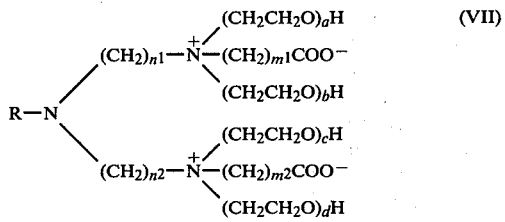

(VII)

that is, in an aqueous solution with at least one alkali metal salt of an ω-halocarboxylic acid of the formula $X(CH_2)_{m1(m2)}COOH$ (VI). The alkali metal salts, and, in particular, the sodium salts, of chloroacetic, chloropropionic, bromoacetic and chloro-n-butyric acid may be mentioned as preferred. If appropriate, halocarboxylic acid and alkali metal hydroxide can be added separately, the salt forming in situ. This reaction is carried out at a temperature of 80° to 100° C. with a 5 to 10% excess of halocarboxylic acid.

The remaining free amino group in the bis-betaine of the formula (VII) so obtained is subsequently oxidized at a temperature of 70° to 90° C. with 70% hydrogen peroxide used in a 5 to 10% molar excess to give the bis-betaine-amine oxide of the formula I.

Advantageously, the bis-betaine-amine oxides of the formula I according to the invention are prepared as 30 to 40 weight % aqueous formulations by suitably adjusting the water content in the final reaction step.

The bis-betaine-amine oxides of the invention as defined in the above formula I are surfactants of mild and weakly degreasing action, and thus excellently suitable for use in cosmetic cleaning agents, i.e. body cleaning agents such as foam baths, shower baths, foot and hand washes or intimate washes and also in hair washes. On use in body cleaning agents a marked improvement in the way the skin feels after the application is achieved, and on use in shampoos there is an improvement in the combability not only of dry but also of wet hair with a simultaneous softening effect, which manifests itself in the hair by a pleasant handle.

The bis-betaine-amine oxides according to the invention can be used in such liquid, pulverulent or aerosoltype cosmetic cleaning agents, in particular in hair washes, not only alone but also combined with anionic, cationic, non-ionic and amphoteric surfactants customarily used in such agents. Examples of anionic surfactants which are suitable for this purpose are soap, fatty alcohol sulfates, alkyl ether sulfates, fatty acid condensation products, such as taurides, methyltaurides and sarcosides, also α-olefin- sulfonates, hydroxyalkanesulfonates, secondary alkanesulfonates, amide ether sulfates and alkylbenzene-sulfonates. Examples of compounds which can be used as non-ionic surfactants are polyglycol monoalkyl ethers and monoesters, amine oxides and ethylene oxide/propylene oxide condensation products. In addition, the combination with other amphoteric surfactants, such as alkylbetaines, alkylamidobetaines, imidazoline derivatives or sulfobetaines, is also possible. The bis-betaine-amine oxides of the invention can furthermore be used in admixture with cationic surfactants, such as cetyltrimethylammonium chloride, cetyltrimethylammonium bromide, pentaoxyethylstearyl-ammonium chloride, quaternized ether-amines or polymeric quaternary ammonium compounds. Further additives which are used in customary manner in cosmetic cleaning agents can be combined with the bis-betaine-amine oxides. Examples of these additives are viscosity-increasing or viscosity-decreasing compounds such as cellulose ethers, electrolytes, such as, for example, sodium chloride or ammonium chloride, fatty acid polyglycol esters, alkanol-amides, magnesium aluminum silicates, polyglycols, glycerol and ethanol. Further additives which can be used are perfume oils and special fragrances, antiseptic agents, dandruff-removing or fungus-killing agents, superfatting agents, preservatives, dyestuffs and nacreous substances. Filler and carrier substances which are customarily used, such as highly disperse and amorphous silica, sodium sulfate, magnesium aluminum silicate, starch derivatives and the like, can also be used in the processing to give pulverulent formulations. Finally, customary propellant gases can also be admixed in the case of aerosol-type formulations. Control of the intended pH value can be effected with inorganic or organic acids or alkalis.

Furthermore, the bis-betaine-amine oxides of the invention are suitable for formulating industrial cleaning agents, i.e. foam cleaners for textile surfaces, such as carpet cleaners, or, in particular, cleaning agents for hard surfaces, such as for example, washing-up liquids, bottle-rinsing agents, floor cleaners, sanitary cleaners or so-called all-purpose cleaning agents. The bis-betaine-amine oxides of the invention are finally suitable as agents for washing textiles. In these possible applications, too, the above anionic, cationic, non-ionic or amphoteric surfactants can be admixed. Chelating agents and, if appropriate, also plastics dispersions can be added as customary auxiliaries to industrial cleaning agents. Other additives which are customary for this purpose are bleaching agents, chlorine donors or other disinfectants. To improve the abrasion effect, suitable additives are chalk, highly disperse amorphous silica, phosphates and plastics. To improve the fat- and soil-solubilizing properties, solvents such as universal spirit or isopropyl alcohol or other cleaning-promoting agents can also be added. Finally, washing agents contain customary builder substances.

A particular application advantage of using the bis-betaine-amine oxides in industrial and cosmetic cleaning agents is their physical and especially chemical stability, for example to electrolytes even when present in a high concentration, to bleaching agents such as are present in sanitary cleaners, to strong alkalis such as incorporated in bottle or oven cleaners, or to oxidants such as are present for example in permanent wave formulations. For example, it is possible to prepare shampoos which have an acid pH value and a long shelf life from the bis-betaine-amine oxides of the invention without, as is the case with customarily used anionic alkylsulfates or alkyl ether sulfates, decomposition by hydrolysis occurring.

The content of bis-betaine-amine oxides according to the invention in such formulations is usually 0.5 to 40% by weight.

The following examples illustrate the invention in more detail:

PREPARATION EXAMPLES

EXAMPLE 1

670 g of coconut fatty amine (mol % composition in respect of the R radicals: $C_8$ 6%, $C_{10}$ 6%, $C_{12}$ 54%, $C_{14}$ 18%, $C_{16}$ and $C_{18}$ 8%), 68 g of water, 34 g of methanol and 14 g of concentrated acetic acid are heated to 60° C. in a 2 liter four-necked flask equipped with a reflux condenser, thermometer, stirrer and metering vessel. 373 g of acrylonitrile are added dropwise within one hour, and the mixture is stirred for a further 24 to 36 hours at 75° C. under reflux. The mixture is then neutralized with 13 g of NaOH and 120 g of water, the wash water is separated and the product is freed from residual water and solvent in vacuo. 1,000 g of coconut-aminodipropionitrile (yield: 95.9%) are obtained.

A 5 liter autoclave is charged with 2,020 g of coconut-aminodipropionitrile, 3 g of supported cobalt catalyst (support: kieselguhr) and 300 ml of liquid ammonia. The hydrogenation takes 3 hours under 150 to 180 bar of $H_2$ and at 110° to 140° C. After the catalyst has been filtered off, 2,010 g of a product which contains 85 to 95% of bis-(3-aminopropyl)-coconut-amine are obtained.

954 g of bis-(3-aminopropyl)-coconut-amine are heated with stirring to 130° C. in a 2 liter pressure vessel equipped with a thermometer, stirrer and an inlet and outlet for ethylene oxide. 667 g of ethylene oxide are added under a pressure of 1 to 3 bar. The increase in weight after a reaction time of 3 hours corresponds to a condensation product of the triamine with 4 to 5 mols of ethylene oxide. 1,605 g of this ethoxylate (99%) are obtained.

237 g of this bis-(3-aminopropyl)-coconut-aminoethoxylate and 609 g of water are introduced into a 2 liter reaction vessel and heated with stirring to 90° C. 110 g of sodium chloroacetate are added at this temperature within 1 hour, and the mixture is stirred for a further 12 hours at 95° C. The bis-betaine-amine oxide of the invention is obtained by subsequent addition of 43 g of 70% by weight hydrogen peroxide and a further reaction time of 8 hours at 80° C. in the form of a 30% by weight aqueous solution.

EXAMPLE 2

670 g of laurylamine ($C_{12}$-fraction: 73 mol %, $C_{14}$-fraction: 23 mol %) are reacted in the manner described in Example 1 with 373 g of acrylonitrile in 68 g of water, 34 g of methanol and 14 g of concentrated acetic acid, and subsequently hydrogenated.

After the hydrogenation, 2,020 g of bis-(3-aminopropyl)-laurylamine are obtained. 954 g of this triamine are condensed with 640 g of ethylene oxide. 1,590 of bis-(3-aminopropyl)-laurylamine ethoxylate (99%) are obtained. 257 g of this ethoxylate and 655 g of water are reacted with 116.5 g of sodium chloroacetate, and subsequently with 48.6 g of 70% by weight $H_2O_2$. The bis-betaine-amine oxide is obtained in 1,070 g of a 30% by weight aqueous solution.

EXAMPLE 3

844 g of myristylamine are reacted at 75° C. with 373 g of acrylonitrile in 68 g of water, 34 g of methanol and 14 g of concentrated acetic acid. 1,164 g of myristylaminodipropionitrile are obtained. 2,052 g of the dipropionitrile are hydrogenated in the manner of Example 1 using a cobalt catalyst. 2,045 g of bis-(3-aminopropyl)myristylamine are obtained. 1,095 g of this triamine are condensed with 647 g of ethylene oxide. 1,725 g of bis-(3-aminopropyl)-myristylamine ethoxylate (99%) are obtained. 290 g of this ethoxylate and 733 g of water are reacted with 116.5 g of sodium chloroacetate, and subsequently with 48.6 g of 70% by weight $H_2O_2$. The bis-betaine-amine oxide is obtained in 1,180 g of 30% by weight aqueous solution.

EXAMPLE 4

1,056.0 g of octylamine are reacted at 75° C. with 849.6 g of acrylonitrile in 106 g of water, 53 g of methanol and 21.1 g of concentrated acetic acid. 1,810 g of octyl-aminodipropionitrile are obtained. 1,980 g of the dipropionitrile are hydrogenated in the manner of Example 1 using a cobalt catalyst. 1,970 g of bis-(3-aminopropyl)-octylamine are obtained. 998 g of this triamine are condensed with 845 g of ethylene oxide. 1,840 g of bis-(3-aminopropyl)-octylamine ethoxylate (99%) are obtained. 230 g of this ethoxylate and 593 g of water are reacted with 116.5 g of sodium chloroacetate, and subsequently with 48.6 g of 70% by weight $H_2O_2$. The bis-betaine-amine oxide is obtained in 960 g of a 30% by weight aqueous solution.

EXAMPLE 5

929 g of tallow fatty amine are reacted at 75° C. with 373 g of acrylonitrile in 68 g of water, 34 g of methanol and 14 g of concentrated acetic acid. 1,237 g of tallow-fatty-aminodipropionitrile are obtained and hydrogenated in accordance with Example 1 to give the corresponding amine. 1230 g of bis-(3-aminopropyl)-tallow fatty amine are obtained.

The ethoxylation reaction is carried out in two stages. First, 1,154 g of bis-(3-aminopropyl)-tallow fatty amine are reacted with 647 g (4.7 mols) of ethylene oxide using the method of Example 1. The product is then reacted with a further 5.3 mols of ethylene oxide in the presence of the customary 0.2% by weight, relative to the amine, of aqueous sodium hydroxide solution (50% strength), so that the total increase in weight corresponds to a condensation product of the triamine with 10 mols of ethylene oxide. 300 g of this ethoxylate and 756 g of water are reacted with 116.5 g of sodium chloroacetate, and subsequently with 48.6 g of 70 weight % $H_2O_2$. The bis-betaine-amine oxide is obtained in 1,216 g of a 30% by weight aqueous solution.

The analytical data of the bis-betaine-amine oxides of the invention, and of their precursors, are summarized in Table I.

Bis-betaine-amine oxide:
The total chlorine content is determined after a Parr digestion with $Na_2O_2$, and ionic chlorine is determined by Volhard titration. The amine oxide content is determined by redox titration with Ti(III) chloride/$NH_4Fe(SO_4)_2.6 H_2O$.

The application examples which follow illustrate the ways bis-betaine-amine oxides can be used for the manufacture of mild cleaning agents. The amounts and percentages in the examples are by weight unless otherwise stated.

EXAMPLE 1A

| Every day shampoo | |
|---|---|
| Bis-betaine-amine oxide of the formula I, prepared according to Example 1 | 15.0% |
| Hydroxyethyl cellulose ether | 1.3% |
| Perfume oil | 0.2% |
| Water, preservative, dyestuff | to 100.0% |

EXAMPLE 2A

| Shampoo for dry hair | |
|---|---|
| Bis-betaine-amine oxide of the formula I, prepared according to Example 1 | 10.0% |
| Sodium salt of lauryldiglycol-ether sulfate | 5.0% |
| Polyethyleneglycol-6000-distearate | 5.0% |
| Water, preservative, dyestuff | to 100.0% |

TABLE I

| Example (Alkyl radical) | Alkylamino-dipropionitrile | | Bis(3-aminopropyl)-alkylamine | | | | Ethoxylate | | Bis-betaine-amine oxide | | |
|---|---|---|---|---|---|---|---|---|---|---|---|
| | AN | tert. N (%) | AN | prim. N (%) | sec. N (%) | tert. N (%) | AN | tert. N (%) | $\Sigma a + b + c + d$ equiv. EO* per mol | total chlorine weight % | ionogenic chlorine weight % | content weight % |
| 1 (coconut) | 34.3 | 94 | 97.3 | 66.2 | 3.3 | 30.5 | 57.5 | >98 | 4.9 | 3.5 | 3.4 | 29.4 |
| 2 (lauryl) | 34.4 | 95 | 97.5 | 65.9 | 2.9 | 31.2 | 58.3 | >98 | 4.7 | 3.5 | 3.4 | 29.5 |
| 3 (myristyl) | 29.2 | 94 | 82.2 | 65.5 | 3.5 | 31.0 | 51.7 | >98 | 4.9 | 3.4 | 3.3 | 29.1 |
| 4 (octyl) | 42.7 | 94 | 120.2 | 65.1 | 3.0 | 31.9 | 65.1 | >98 | 4.8 | 3.6 | 3.5 | 29.4 |
| 5 (tallow fat) | 27.4 | 94 | 78.0 | 66.1 | 2.6 | 31.3 | 50.0 | >98 | 4.9 | 3.0 | 3.0 | 29.9 |

*EO = Ethylene oxide

The above data are determined as follows:

Alkylaminodipropionitrile:

The amine number (AN) and the tertiary nitrogen content are determined by titration with 0.1 N $HClO_4$ in glacial acetic acid or acetic anhydride. The amine number is given by $$AN = \frac{\text{ml of 0.1 N } HClO_4}{\text{original sample weight in g}}$$

Bis-(3-aminopropyl)-alkylamine:

The amine number and the distribution of the amine are determined by titration with 0.2 N solution of HCl in isopropanol in an anhydrous medium. The distribution of amine is carried out by blocking the basic amine-nitrogen with salicylaldehyde (primary N) and phenyl isothiocyanate (primary and secondary N) respectively.

Ethoxylate:

The amine number and the tertiary nitrogen content are determined by titration with 0.1 N $HClO_4$ in glacial acetic acid or acetic anhydride. The mols of ethylene oxide absorbed are calculated from the amine numbers or from the increase in mass compared to the previous stage.

EXAMPLE 3A

| Shower bath | |
|---|---|
| Bis-betaine-amine oxide of the formula I, prepared according to Example 1 | 8.0% |
| Disodium salt of coconut-triglycol ether sulfosuccinate | 6.0% |
| Hydroxyethyl cellulose ether | 1.2% |
| Coconut fatty acid monoethanolamide | 1.0% |
| Water, preservative, perfume oil | to 100.0% |

EXAMPLE 4A

| Intimate wash | |
|---|---|
| Bis-betaine-amine oxide of the formula I, prepared according to Example 1 | 10.0% |
| Coconutethylcycloimidino-1-hydroxy-3-ethyl-sodium alcoholate-2-methylsodium carboxylate | 5.0% |
| Citric acid | 0.2% |
| Bacteriostatic agent, perfume oil, water | to 100.0% |

EXAMPLE 5A

| Hand wash | |
|---|---|
| Bis-betaine-amine oxide of the formula I, prepared according to Example 1 | 10.0% |
| Sodium salt of secondary alkanesulfonate (alkene radical $C_{13}$-$C_{17}$) | 5.0% |
| Coconut fatty acid diethanolamine | 2.0% |
| Water, consistency agent, perfume oil | to 100.0% |

EXAMPLE 6A

| Acidic shampoo | |
|---|---|
| Bis-betaine-amine oxide of the formula I, prepared according to Example 2 | 7.0% |
| Acylaminoglycol ether sulfate-triethanol-amine salt (acyl = caprylic to stearic acid radical) | 5.0% |
| Sodium salt of lauroylsarcoside | 2.0% |
| Citric acid | 0.45% |
| Consistency agent, dyestuff, preservative, water, perfume oil | to 100.0% |

EXAMPLE 7A

| Foam bath | |
|---|---|
| Bis-betaine-amine oxide of the formula I, prepared according to Example 2 | 20.0% |
| Laurylsulfate-triethanolamine salt | 5.0% |
| Lauryl alcohol, condensed with 10 mols of ethylene oxide | 3.0% |
| Oleic acid ethanolamide | 1.0% |
| Water | to 100.0% |

EXAMPLE 8A

| Foam bath | |
|---|---|
| Bis-betaine-amine oxide of the formula I, prepared according to Example 1 | 35.0% |
| Coconut fatty acid diethanolamide | 2.0% |
| Perfume oil | 1.0% |
| Water | to 100.0% |

EXAMPLE 9A

| Baby shampoo | |
|---|---|
| Bis-betaine-amine oxide of the formula I, prepared according to Example 2 | 12.0% |
| Caprylic/capric acid triglyceride | 3.0% |
| Camomile extract | 0.1% |
| Water, preservative | to 100.0% |

EXAMPLE 10A

| Industrial cleaning agent | |
|---|---|
| Bis-betaine-amine oxide of the formula I, prepared according to Example 1 | 20.0% |
| Isopropyl alcohol | 5.0% |
| Urea | 5.0% |
| Water, perfume oil | to 100.0% |

In order to determine the gentle cleaning action, the surfactants of the invention were examined in the following in vitro tests:

(1) Pigment washing power in a Launder-O-Meter

In this test, a Launder-O-Meter (manufacturer: Atlas Electric Devices, Chicago 13, USA) was used as apparatus. A woolen fabric of the Laundry Research Institute, Krefeld, West-Germany, which was soiled with mineral oil and iron oxides, was washed under the following defined conditions:

| | |
|---|---|
| Surfactant concentration | 0.5 and 1% |
| Water | 15° German Hardness |
| Washing temperature | 40° C. |
| Washing time | 10 minutes |
| Mechanism | 10 steel balls |

After having carried out the washing tests, the wool specimens were dried on a calender, and the reflectance was determined by means of an Elrepho apparatus for measuring the degree of whiteness.

$$\% \text{ reduction} = \frac{(\text{reflectance value} - \text{blank value})}{\text{max. reflectance} - \text{blank value}} \times 100$$

The corresponding data are listed in Table II. They demonstrate that the bis-betaine-amine oxides have a considerably gentler detergent action than the standard surfactants.

(2) Solubilizing test using isopropyl myristate

In addition to the dispersion of the particles in the aqueous phase, the solubilization or emulsification of oily impurities is important for the cleaning of soiled surfaces. In order to characterize the solubilizing power of surfactants, isopropyl myristate solution dyed red was stirred into a 10% aqueous solution containing a surfactant; after stirring for 60 minutes at 300 rpm, the solution or emulsion was stored at 20° C. in a separating funnel. Subsequently, the amount of solubilized isopropyl myristate was determined by colorimetry from the lower, clear phase.

Table III shows the low solubilizing power of the bis-betaine-amine oxides as compared to the commercial substances having a heavily detergent action.

TABLE II

| Product (1% active substance) | % reduction |
|---|---|
| Sodium salt of alkylbenzenesulfonate | 79.5 |
| Lauryldimethyl-amine oxide | 62.4 |
| Sodium salt of laurylsulfate | 46.1 |
| Coconutamidobetaine | 74.1 |
| Bis-betaine-amine oxide (of invention) | 16.2 |

TABLE III

| Product (10% active substance in isopropyl myristate) | g of solubilized isopropyl myristate |
|---|---|
| Sodium salt of alkylbenzenesulfonate | 2.450 |
| Lauryldimethylamine oxide | 3.263 |
| Sodium salt of laurylsulfate | 2.831 |
| Coconutamidobetaine | 1.266 |
| Bis-betaine-amine oxide (of invention) | 0.081 |

What is claimed is:
1. Bis-betaine-amine oxides of the formula

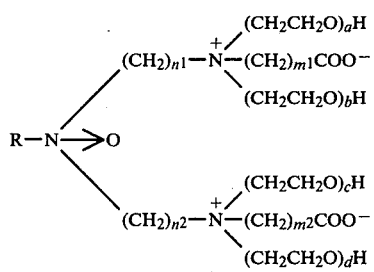

(I)

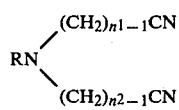

(III)

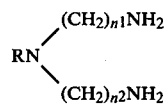

(IV)

in which
R is a saturated or an olefinically unsaturated hydrocarbon radical having 1 to 3 double bonds and 8 to 22 carbon atoms,
$n^1$ and $n^2$ each is an integer of from 2 to 3, $n^1$ and $n^2$ optionally being identical or different,
$m^1$ and $m^2$ each is an integer of from 1 to 4, $m^1$ and $m^2$ optionally being identical or different, and
a, b, c and d, being identical or different, each is a number of from 1 to 5, with the proviso that the sum $(a+b+c+d)$ is at most 10.

2. A process for the preparation of bis-betaine-amine oxides as claimed in claim 1, in which first a primary amine of the formula $RNH_2$ (II) is reacted with 2 mols of at least one reactive nitrile of 2 to 3 carbon atoms to give a compound of the formula which is reduced in the presence of hydrogen to a compound of the formula which is condensed with ethylene oxide to give a compound of the formula

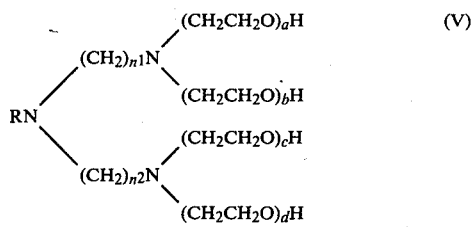

(V)

which process comprises quaternizing this compound of the formula (V) in an aqueous solution with at least one alkali metal salt of a ω-halocarboxylic acid of the formula

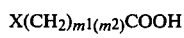

$X(CH_2)_{m1(m2)}COOH$ (VI)

to give a bis-betaine of the formula

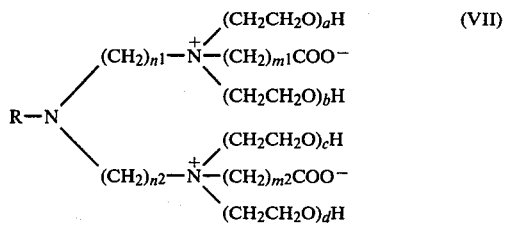

(VII)

and then oxidizing the bis-betaine obtained with hydrogen peroxide to yield the bis-betaine amine oxide.

3. A cosmetic cleaning agent, containing water as liquid carrier, at least one surfactant from the group consisting of anionic, cationic, non-ionic and amphoteric surfactants, customary cosmetic additives and auxiliaries, which comprises a surface active effective amount of a bis-betaine amine oxide as claimed in claim 1.

4. An industrial cleaning agent, containing water as liquid carrier, at least one surfactant from the group consisting of anionic, cationic, non-ionic and amphoteric surfactants and cleaning-promoting additives and customary auxiliaries, which comprises a surface active effective amount of a bis-betaine-amine oxide as claimed in claim 1.

* * * * *